United States Patent

Fushimi et al.

[11] Patent Number: 6,063,727
[45] Date of Patent: May 16, 2000

[54] CATALYST FOR OLEFIN POLYMERIZATION AND METHOD FOR PREPARING POLYOLEFINS

[75] Inventors: Masaki Fushimi, Oita; Toshio Fujita, Tokyo; Shintaro Inazawa, Oita, all of Japan

[73] Assignee: Japan Polyolefins Co., Ltd., Tokyo, Japan

[21] Appl. No.: 08/868,673

[22] Filed: Jun. 4, 1997

[30]  Foreign Application Priority Data

Dec. 19, 1996 [JP] Japan .................................. 8-339796
Dec. 19, 1996 [JP] Japan .................................. 8-339797

[51] Int. Cl.$^7$ ..................................................... B01J 31/00
[52] U.S. Cl. ............................ 502/125; 502/126; 526/128
[58] Field of Search ..................................... 502/125, 126

[56]  References Cited

U.S. PATENT DOCUMENTS

| | | | |
|---|---|---|---|
| 4,952,649 | 8/1990 | Kioka et al. | 526/125.3 |
| 5,407,883 | 4/1995 | Fushimi et al. | 502/125 |
| 5,476,825 | 12/1995 | Fushimi et al. | 502/125 |

OTHER PUBLICATIONS

Brewita, Organic Chemistry, Prentice–Hall, hr. N.Y, 1948, pp. 34–35.

*Primary Examiner*—David W. Wu
*Assistant Examiner*—Ling-Siu Choi
*Attorney, Agent, or Firm*—Sughrue, Mion, Zinn, Macpeak & Seas, PLLC

[57]  ABSTRACT

Disclosed are a catalyst for polymerizing olefins containing a solid catalyst component containing titanium, magnesium and halogen as essential components (component (A)); an organic aluminum compound (component (B)); and a silane compound (component (C)) represented by general formula (1)

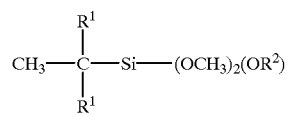

(1)

wherein $R^1$ and $R^2$ independently represent a straight, branched or cyclic saturated aliphatic hydrocarbon group or a silyl group, a method of preparing polyolefins using the catalyst as well as novel trimethoxysilane compounds represented by the general formula (1) in which $R^1$ is a straight saturated aliphatic hydrocarbon group having 2 to 10 carbon atoms, and $R^2$ represents a methyl group. Use of the catalyst enables efficient production of polyolefins having a low molecular weight (MFR>20 (g/10 minutes)), a broad molecular weight distribution (MLMFR/MFR>22) and a high stereoregularity when applied to polymerization of olefins having 3 or more carbon atoms.

4 Claims, No Drawings

CATALYST FOR OLEFIN POLYMERIZATION AND METHOD FOR PREPARING POLYOLEFINS

FIELD OF THE INVENTION

The present invention relates to a catalyst for olefin polymerization. More particularly, the present invention relates to a catalyst for the preparation of polyolefins which catalyst comprises a silicon compound capable of providing polyolefins having high stereoregularity in high yields, to a method for preparing polyolefins with such a catalyst, as well as to a novel trimethoxysilane compound useful as a component of the catalyst.

BACKGROUND OF THE INVENTION

It is known that use of silicon compounds as the cocatalyst component in a carried-type Ziegler catalyst increases the stereoregularity of the resulting polymer, thus increasing the working characteristics of the polymer.

Such silicon compounds include, for example, diphenyldimethoxysilane compounds (EP45975 (Published Unexamined Japanese Patent Application Nos. 57-63310 and 57-63311), Published Unexamined Japanese Patent Application Nos. 58-138708, 61-296006, WO8805056 (Published Unexamined Japanese Patent Application No. 63-175008), and EP283011 (Published Unexamined Japanese Patent Application No. 63-289004), diisobutyldimethoxysilane compounds (Published Unexamined Japanese Patent Application No. 62-18406, EP250229 (Published Unexamined Japanese Patent Application No.63-258907), Published Unexamined Japanese Patent Application No. 2-70708, EP376145 (Published Unexamined Japanese Patent Application No. 2-173010), and Published Unexamined Japanese Patent Application No. 3-33103), diisopropyldimethoxysilane compounds (Published Unexamined Japanese Patent Application No. 63-258907, EP350170 (Published Unexamined Japanese Patent Application No. 2-229807), Published Unexamined Japanese Patent Application Nos. 3-33102 and 3-33103), dicyclopentyldimethoxysilane compounds (Published Unexamined Japanese Patent Application No. 2-229807), di-t-butyldimethoxysilane compounds (EP349772 (Published Unexamined Japanese Patent Application No. 2-70708), Published Unexamined Japanese Patent Application Nos. 2-229806 and 3-33102), dicyclohexyldimethoxysilane compounds (Published Unexamined Japanese Patent Application No. 63-258907), cyclohexylmethyldimethoxysilane compounds (Published Unexamined Japanese Patent Application Nos. 2-170803 and 2-229807), cyclohexylethyldimethoxysilane compounds (EP376084 (Published Unexamined Japanese Patent Application No. 2-163104)), t-butylmethyldimethoxysilane compounds (Published Unexamined Japanese Patent Application Nos. 62-11705, 62-20507, 63-92615, and 2-229807), t-butylpropyldimethoxysilane compounds (Published Unexamined Japanese Patent Application Nos. 4-202505 and 5-17319), phenyltriethoxysilane compounds (Published Unexamined Japanese Patent Application No. 57-63311, DE895019 (Published unexamined Japanese Patent Application No. 58-83006), Published Unexamined Japanese Patent Application Nos. 62-20507 and 61-296006), ethyltriethoxysilane compounds (Published Unexamined Japanese Patent Application No. 57-63310), butyltriethoxysilane compounds (Published Unexamined Japanese Patent Application No. 2-170803), t-butyltrimethoxysilane compounds (Published Unexamined Japanese Patent Application Nos. 62-11705, 63-92615, 63-258907, 3-33106, 3-33105, and 2-70708), t-butyl(t-butoxy)dimethoxysilane compounds (EP419249 (Published Unexamined Japanese Patent Application No. 3-119004)), isobutyltrimethoxysilane compounds (Published Unexamined Japanese Patent Application No. 3-33106), t-butyltriethoxysilane compounds (Published Unexamined Japanese Patent Application No. 2-229807), norbornanetrimethoxysilane compounds (Published Unexamined Japanese Patent Application No. 63-92615) and the like.

However, compounds having benzene rings connected to a silicon atom, such as diphenyldimethoxysilane compounds, will upon decomposition release benzene which is harmful to humans and which remains in the polymers resulting from such compounds. This causes a serious hygienic problem.

While diisopropyldimethoxysilane, dicyclopentyldimethoxysilane, dicyclohexyldimethoxysilane, di-t-butyldimethoxysilane, t-butyl(t-butoxy)dimethoxysilane, t-butylmethyldimethoxysilane compounds and the like have aliphatic hydrocarbyl groups on silicon atoms so that there arises no problem from the viewpoint of hygiene but presence of bulky substituents connected to silicon atoms leads to difficulties in their synthesis as well as to high costs.

Diisobutyldimethoxysilane, cyclohexylmethyldimethoxysilane and cyclohexylethyldimethoxysilane compounds can be synthesized by hydrosilylation reaction so that they can be prepared at low costs. However, the stereoregularity itself does not always suffice the requirements for the polymers.

On the other hand, trialkoxysilane compounds, for example, phenyltriethoxysilane, ethyltriethoxysilane, butyltriethoxysilane, t-butyltrimethoxysilane, isobutyltrimethoxysilane, t-butyltriethoxysilane, norbornanetrimethoxysilane and the like, are known to deactivate the activity of catalysts considerably. Hence, in order to prevent the reduction in the activity of catalysts when the trimethoxysilane compounds are used, there have been proposed several technologies which use a dimethoxysilane compound in combination with the trimethoxysilane compounds (Published Unexamined Japanese Patent Application No. 2-70708, 3-33103, 3-33105, and 3-33106). However, each of these causes new problems; for example, they each result in the reduction of stereoregularity and require a plurality of tanks for storing respective silane compounds and feeding them to the plant.

Recently, there have been disclosed methods for preparing low molecular weight polyolefins with trialkoxysilane compounds having a 1-alkylcycloalkyl group (Published Unexamined Japanese Patent Application No. 8-157520 and 8-59730). However, in the case of magnesium chloride-carried catalysts containing trialkoxysilane compounds as a co-catalyst component, it has been difficult to obtain polyolefins having a low molecular weight (MFR>20(g/10 minutes)), a broad molecular weight distribution (MLMFR/MFR>22), and a high stereoregularity, which are suitable for articles obtained by inflation molding or blow molding.

Therefore, an object of the present invention is to solve the above-described problems in preparing polyolefins with a carried-type Ziegler catalyst according to the prior art and provide an olefin polymerization catalyst and a method for the preparation of polyolefins therewith which can, when applied to polymerization of olefins having 3 or more carbon atoms, give, in high yields, highly stereoregular polyolefins having a low molecular weight (MFR>20 (g/10 minutes) and a broad molecular weight distribution (MLMFR/MFR>22).

SUMMARY OF THE INVENTION

In order to solve the above-described problems, the present inventors have made intensive research on the development of co-catalysts for carried-type Ziegler catalysts, particularly on external donor components comprising electron donating compounds. As a result, it was found that polymerization of olefins in the presence of a catalyst comprising (i) a solid catalyst component containing titanium, magnesium, and halogen as essential ingredients (component (A)), (ii) and an organic aluminum compound (component (B)), and a specified silane compound as an external donor compound having electron donating capability (component (C)) affords practically useful polyolefins having a low molecular weight, a broad molecular weight distribution, and a high stereoregularity. The present invention has been completed based on this discovery.

To note, the trimethoxysilane compounds included in the specified silane compounds useful in the catalyst component (C) in the present invention are novel compounds.

That is, the present invention provides the following olefin polymerization catalysts, methods for preparing polyolefins, and novel trimethoxysilane compounds.

1) A catalyst for polymerizing olefins, comprising:
(A) a solid catalyst component comprising titanium, magnesium and halogen as essential ingredients;
(B) a n organic aluminum compound; and
(C) a silane compound represented by general formula (1)

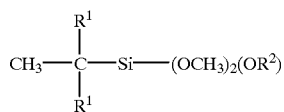

(1)

wherein $R^1$ is a straight chain saturated aliphatic hydrocarbon group having 2 or more carbon atoms, a branched or cyclic saturated aliphatic hydrocarbon group having 3 or more carbon atoms or a silyl group; and $R^2$ is a straight chain, branched or cyclic saturated hydrocarbon group.

2) The catalyst as described in 1) above, wherein said silane compound is a compound represented by the general formula (1) in which $R^1$ is a straight chain saturated aliphatic hydrocarbon group having 2 to 10 carbon atoms, a branched or cyclic saturated aliphatic hydrocarbon group having 3 to 10 carbon atoms or a trialkylsilyl group; and $R^2$ is a straight chain saturated hydrocarbon group having 1 to 10 carbon atoms or a branched saturated aliphatic hydrocarbon group having 3 to 10 carbon atoms.

3) The catalyst as described in 1) or 2) above, wherein said silane compound is a silane compound selected from the group consisting of:
3-methyl-3-(trimethoxysilyl)pentane,
3-methyl-3-(tert-butoxydimethoxysilyl)pentane,
4-methyl-4-(trimethoxysilyl)heptane,
2,3,4-trimethyl-3-(trimethoxysilyl)pentane,
3,4,5-trimethyl-4-(trimethoxysilyl)heptane,
1,1-dicyclopentyl-1-(trimethoxysilyl)ethane,
1,1-dicyclohexyl-1-(trimethoxysilyl)ethane, and
1,1-bis(trimethylsilyl)-1-(trimethoxysilyl)ethane.

4) A method of preparing a polyolefin having an MFR>20 (g/10 minutes) and an MLMFR/MFR>22, comprising the step of:
polymerizing an olefin in the presence of the catalyst as described in any of 1) to 3) above.

5) A trimethoxysilane compound represented by general formula (6)

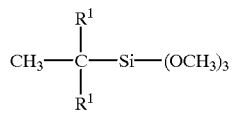

(6)

wherein $R^1$ is a straight chain saturated aliphatic hydrocarbon group having 2 to 10 carbon atoms or a branched or cyclic saturated aliphatic hydrocarbon group having 3 to 10 carbon atoms.

6) The trimethoxysilane compound as described in 5) above, wherein $R^1$ is a straight chain saturated aliphatic hydrocarbon having 2 to 10 carbon atoms.

7) 3-Methyl-3-(trimethoxysilyl)pentane represented by formula (7).

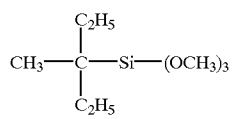

(7)

Hereinafter, the present invention will be described more concretely.

Component (A)

Solid catalyst component containing titanium, magnesium and halogen as essential ingredients The magnesium component which can be used in the present invention includes, for example, magnesium halides such as magnesium chloride and magnesium bromide; alkoxymagnesiums such as ethoxymagnesium and isopropoxymagnesium; magnesium carboxylates such as magnesium laurate and magnesium stearate; alkylmagnesiums such as butylethylmagnesium; and the like. Mixtures of two or more of these compounds may also be used. Preferred are those components which contain magnesium halides or those which form magnesium halides when catalysts are formed, and more preferably, those components in which the halogen is chlorine.

Examples of the titanium component which can be used in the present invention include titanium halides such as titanium tetrachloride and titanium trichloride; titanium alkoxides such as titanium butoxide and titanium ethoxide; aryloxytitanium halides such as phenoxytitanium chloride; and the like. Mixtures of two or more of these compounds may also be used.

The halogen-containing component which can be used in the present invention includes, for example, those compounds containing halogen selected from fluorine, chlorine, bromine or iodine, preferably chlorine, specific examples of such compounds include titanium halides such as titanium tetrachloride and titanium tetrabromide; silicon halides such as silicon tetrachloride and silicon tetrabromide; phosphorus halides such as phosphorus trichloride and phosphorus pentachloride; and the like. For some preparation methods, there can also be used halogenated hydrocarbons, halogen molecules, hydrohalogenic acid such as HCl, HBr and HI. The halogen-containing component may include the same compounds as the above-described titanium compounds or magnesium compounds.

Upon preparation of the solid catalyst component (A), various electron donors (internal donors) may be added. The addition of such is preferred. As the electron donors, there can be exemplified oxygen-containing compounds, nitrogen-containing compounds and the like.

More specifically, there can be used:
(1) alcohols having 1 to 20 carbon atoms, such as methanol, ethanol, propanol, butanol, heptanol, hexanol, octanol, dodecanol, octadecyl alcohol, 2-ethylhexyl alcohol, benzyl alcohol, cumyl alcohol, diphenylmethanol, triphenylmethanol, and the like;
(2) phenols having 6 to 25 carbon atoms which may have an alkyl group on the benzene ring, such as phenol, cresol, ethylphenol, propylphenol, cumylphenol, nonylphenol, naphthol, and the like;
(3) ketones having 3 to 15 carbon atoms, such as acetone, methyl ethyl ketone, methyl isobutyl ketone, acetophenone, cyclohexanone, and the like;
(4) aldehydes having 2 to 15 carbon atoms, such as acetaldehyde, propionaldehyde, tolualdehyde, naphthoaldehyde, and the like;
(5) organic acid esters having 2 to 20 carbon atoms, such as methyl formate, ethyl formate, methyl acetate, ethyl acetate, propyl acetate, octyl acetate, cyclohexyl acetate, methylcellosolve acetate, cellosolve acetate, ethyl propionate, methyl n-butyrate, methyl isobutyrate, ethyl isobutyrate, isopropyl isobutyrate, ethyl valerate, butyl valerate, ethyl stearate, methyl chloroacetate, ethyl dichloroacetate, methyl methacrylate, ethyl methacrylate, ethyl crotonate, ethyl cyclohexanecarboxylate, methyl phenylacetate, methyl phenylbutyrate, propyl phenylbutyrate, methyl benzoate, ethyl benzoate, propyl benzoate, butyl benzoate, octyl benzoate, cyclohexyl benzoate, phenyl benzoate, benzyl benzoate, cellosolve benzoate, methyl toluylate, ethyl toluylate, amyl toluylate, ethyl ethylbenzoate, methyl anisate, ethyl anisate, ethyl ethoxybenzoate, diethyl phthalate, diisobutyl phthalate, diheptyl phthalate, dineopentyl phthalate, γ-butyrolactone, γ-valerolactone, cumarine, phthalide, diethyl carbonate, methyl orthoformate, and the like;
(6) alkoxy esters, such as methyl methoxyacetate, ethyl methoxyacetate, butyl methoxyacetate, phenyl methoxyacetate, methyl ethoxyacetate, ethyl ethoxyacetate, butyl ethoxyacetate, phenyl ethoxyacetate, ethyl n-propoxyacetate, ethyl i-propoxyacetate, methyl n-butoxyacetate, ethyl i-butoxyacetate, ethyl n-hexyloxyacetate, octyl sec-hexyloxyacetate, methyl 2-methylcyclohexyloxyacetate, methyl 3-methoxypropionate, ethyl 3-methoxypropionate, butyl 3-methoxypropionate, ethyl 3-ethoxypropionate, butyl 3-ethoxypropionate, n-octyl 3-ethoxypropionate, dodecyl 3-ethoxypropionate, pentamethylphenyl 3-ethoxypropionate, ethyl 3-(i-propoxy)propionate, butyl 3-(i-propoxy)propionate, allyl 3-(n-propoxy)propionate, cyclohexyl 3-(n-butoxy)propionate, ethyl 3-neopentyloxypropionate, butyl 3-n-octyloxy)propionate, octyl 3-(2,6-dimethyldecyloxy)propionate, ethyl 4-ethoxybutyrate, cyclohexyl 4-ethoxybutyrate, octyl 5-(n-propoxy)valerate, ethyl 12-ethoxylaurate, ethyl 3-(1-indenoxy)propionate, methyl 3-methoxyacrylate, methyl 2-ethoxyacrylate, ethyl 3-phenoxyacrylate, ethyl 2-methoxypropionate, n-butyl 2i--propoxy)butyrate, methyl 2-ethoxyisobutyrate, phenyl 2-cyclohexyloxyisovalerate, butyl 2-ethoxy-2-phenylacetate, allyl 3-neopentyloxybutyrate, methyl 3-ethoxy-3-(o-methylphenyl)propionate, ethyl 3-ethoxy-2-(o-methylphenyl)propionate, ethyl 4-ethoxy-2-methyl-1-naphthylnonanoate, ethyl 2-methoxycyclopentanecarboxylate, butyl 2-ethoxycyclohexanecarboxylate, isopropyl 3-(ethoxymethyl)tetralin-2-acetate, ethyl 8-butoxydecaline-1-carboxylate, methyl 3-ethoxynorbornane-2-carboxylate, methyl 2-(phenoxy)acetate, ethyl 3-(p-cresoxy)propionate, methyl 4-(2-naphthoxy)butyrate, butyl 5-carbazoloxyvalerate, methyl 2-phenoxypropionate, ethyl 3-(4-methylphenoxy)-2-phenylpropionate, ethyl 2-phenoxycyclohexanecarboxylate, ethyl thiophene-3-oxyacetate, ethyl 2-(2-picolinoxymethyl)cyclohexanecarboxylate, ethyl 3-furfuryloxypropionate, and the like;
(7) keto esters, such as methyl acetylacetate, ethyl acetylacetate, butyl acetylacetate, methyl propionylacetate, phenyl acetylacetate, methyl propionylacetate, ethyl propionylacetate, phenyl propionylacetate, butyl propionylacetate, ethyl butyrylacetate, ethyl i-butanoylacetate, ethyl pentanoylacetate, methyl 3-acetylpropionate, ethyl 3-acetylpropionate, butyl 3-acetylpropionate, ethyl 3-propionylpropionate, butyl 3-propionylpropionate, n-octyl 3-propionylpropionate, dodecyl 3-propionylpropionate, pentamethylphenyl 3-propionylpropionate, ethyl 3-(i-propionyl)propionate, butyl 3-(i-propionyl)propionate, allyl 3-(i-propionyl)propionate, cyclohexyl 3-(i-propionyl)propionate, ethyl 3-neopentanoylpropionate, butyl 3-n-laurylpropionate, methyl 3-(2,6-dimethylhexanoyl)propionate, ethyl 4-propionylbutyrate, cyclohexyl 4-propionylbutyrate, octyl 5-butyrylvalerate, ethyl 12-butyryllaurate, methyl 3-acetylacrylate, methyl 2-acetylacrylate, ethyl 3-benzoylpropionate, methyl 3-benzoylpropionate, ethyl 3-methylbenzoylpropionate, butyl 3-toluylbutyrate, ethyl o-benzoylbenzoate, ethyl m-benzoylbenzoate, ethyl p-benzoylbenzoate, butyl o-toluylbenzoate, ethyl o-toluylbenzoate, ethyl m-toluylbenzoate, ethyl p-toluylbenzoate, ethyl o-(2,4,6-trimethylbenzoyl)benzoate, ethyl m-(2,4,6-trimethylbenzoyl)benzoate, ethyl p-(2,4,6-trimethylbenzoyl)benzoate, ethyl o-ethylbenzoylbenzoate, ethyl o-acetylbenzoate, ethyl o-propionylbenzoate, ethyl o-laurylbenzoate, ethyl o-cylcohexanoylbenzoate, ethyl o-dodecylbenzoate, and the like;
(8) inorganic acid esters, such as methyl borate, butyl titanate, butyl phosphate, diethyl phosphite, di-(2-phenylphenyl)phosophorochloridate, and the like;
(9) ethers having 2 to 25 carbon atoms, such as dimethyl ether, diethyl ether, diisopropyl ether, dibutyl ether, diamyl ether, tetrahydrofuran, anisole, diphenyl ether, ethylene glycol diethyl ether, ethylene glycol diphenyl ether, 2,2-dimethoxypropane, and the like;
(10) acid amides having 2 to 20 carbon atoms, such as acetamide, benzamide, toluylamide, and the like;
(11) acid halides having 2 to 20 carbon atoms, such as acetyl chloride, benzoyl chloride, toluyl chloride, anisolyl chloride, phthaloyl chloride, isophthaloyl chloride, and the like;
(12) acid anhydrides having 2 to 20 carbon atoms, such as acetic anhydride, phthalic anhydride, and the like;
(13) amines having 1 to 20 carbon atoms, such as monomethylamine, monoethylamine, diethylamine, tributylamine, piperidine, tribenzylamine, aniline, pyridine, picoline, tetramethylethylenediamine, and the like;

(14) nitriles having 2 to 20 carbon atoms, such as acetonitrile, benzonitrile, tolunitrile, and the like;

(15) thiols having 2 to 20 carbon atoms, such as ethyl thioalcohol, butyl thioalcohol, phenyl thiol, and the like;

(16) thioethers having 4 to 25 carbon atoms, such as diethyl thioether, diphenyl thioether, and the like;

(17) sulfates having 2 to 20 carbon atoms, such as dimethyl sulfate, diethyl sulfate, and the like;

(18) sulfonic acids having 2 to 20 carbon atoms, such as phenyl methyl sulfone, diphenyl sulfone, and the like;

(19) silicon-containing compounds having 2 to 24 carbon atoms, such as phenyltrimethoxysilane, phenyltriethoxysilane, phenyltributoxysilane, vinyltriethoxysilane, diphenyldiethoxysilane, phenyldimethylmethoxysilane, phenyldimethylethoxysilane, triphenylmethoxysilane, hexamethyldisiloxane, octamethyltrisiloxane, trimethylsilanol, phenyldimethylsilanol, triphenylsilanol, diphenylsilanediol, lower alkyl silicate (particularly, ethyl silicate), and the like.

Two or more of the electron-donating compounds can be used in combination. Of these, preferred are the organic acid esters, alkoxyesters, and ketoesters.

The preparation method for the solid catalyst component (A) used in the present invention is not limited particularly and there can be used, for example, the following methods.

(a) The method in which magnesium halide, titanium halide and the above-described electron donating compound are made contact each other by pulverizing them together or dispersing or dissolving them in a solvent.

(b) The method in which a complex of magnesium halide and an organic or inorganic compound (which may include the above-described electron donating compound) is made contact with titanium halide or a complex of titanium halide and the above-described electron donating compound.

(c) The method in which a complex of magnesium halide and an organic or inorganic compound (which may include the above-described electron donating compound) is made contact with the above-described electron donating compound and titanium compound sequentially, in this order or in a reversed order.

(d) The method in which a magnesium compound (or a mixture thereof with a titanium compound) is made contact with the above-described electron donating compound and simultaneously or in a later stage is made contact with a titanium compound and/or halogenated, and in which a titanium compound has to be used at least at one of the stages.

The above-described catalyst components may be prepared as carried or impregnated on a substance used as a catalyst carrier, for example, silica, alumina or the like.

Although the quantitative relationship among various components in the component (A) may be set up freely as far as the advantageous effects of the present invention are recognized, generally, the components are used preferably in amounts within the following ranges.

The content of magnesium in the component (A) by atomic ration to titanium may be within the range of 0.1 to 1,000, preferably the range of 2 to 200, and in the case where electron donating compounds are used, their content by atomic ratio to titanium may be 10 or less, preferably within the range of 0.1 to 5.

The average particle diameter of the solid catalyst component which can be used in the present invention may be selected freely as long as the advantageous effects of the present invention are recognizable, but is generally within the range of 0.1 to 200 microns, preferably 1 to 100 microns, and more preferably 10 to 100 microns.

Representative examples of the organic aluminum compound usable in the present invention include those represented by general formulae (2) to (5) below.

(2)

$$AlR^3R^4R^5$$

(3)

$$R^6R^7Al\text{---}O\text{---}AlR^8R^9$$

(4)

$$\left[\underset{|}{\overset{R^{10}}{(Al\text{---}O)_{n+2}}}\right] \text{; and/or}$$

(5)

$$R^{10}\text{---}\underset{|}{\overset{R^{10}}{(Al\text{---}O)_{\overline{n}}}}\text{---}Al(R^{10})_2$$

In the formula (2) above, $R^3$, $R^4$ and $R^5$, which may be the same or different, are hydrocarbon groups containing up to 12 carbon atoms.

In the formula (3) above, $R^6$, $R^7$ and $R^8$, which may be the same or different, are hydrocarbon groups containing up to 12 carbon atoms.

In the formulae (4) and (5) above, $R^{10}$ is a hydrocarbon group having up to 12 carbon atoms and n is an integer of 1 or more.

Representative examples of the organic aluminum compound represented by formula (2) include trialkylaluminums such as trimethylaluminum, triethylaluminum, tripropylaluminum, tributylaluminum, trihexylaluminum, and trioctylaluminum; alkylaluminum hydrides such as diethylaluminum hydride and diisobutylaluminum hydride; and alkylaluminum halides such as diethylaluminum chloride, diethylaluminum bromide, ethylaluminum sesquichloride; and the like.

Among the organic aluminum compounds represented by general formula (3) above, representative examples thereof include alkyldialmoxanes such as tetraethyldialmoxane and tetrabutyldialmoxane.

The general formulae (4) and (5) above represent aluminoxanes, which are polymers of aluminum compounds. $R^{10}$ includes a methyl group, an ethyl group, a propyl group, a butyl group, a benzyl group and the like, with a methyl group and an ethyl group being preferred, and n is preferably 1 to 10.

Among the organic aluminum compounds, preferred are trialkylaluminum, alkylaluminum hydrides and alkylalmoxanes since they exhibit particularly preferable results.

In the polymerization of olefins, the organic aluminum is used in amounts generally $10^{-4}$ mmol/liter or more, preferably $10^{-2}$ mmol/liter or more.

The proportion by mole of the solid catalyst to titanium atom is generally 0.5 or more, preferably 2 or more, and more preferably 10 or more. If the amount of the organic aluminum is too low, the polymerization activity decreases greatly. Note that when the amount of organic aluminum in the polymerization system is 20 mmol/liter or more and its proportion to titanium atom is 1000:1 or more by mole, a further increase in the values of these parameters will give no improvement in the performance of catalyst.

The catalyst component (C) used in the present invention is a silicon compound having the formula represented by the general formula (1)

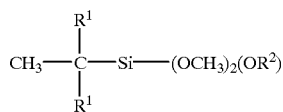

(1)

wherein $R^1$ is a straight chain saturated aliphatic hydrocarbon group having 2 or more carbon atoms, a branched or cyclic saturated aliphatic hydrocarbon group having 3 or more carbon atoms or a silyl group; and $R^2$ is a straight chain, branched or cyclic saturated hydrocarbon group. Preferably, $R^1$ is a straight chain saturated aliphatic hydrocarbon group having 2 to 10 carbon atoms, a branched or cyclic saturated aliphatic hydrocarbon group having 3 to 10 carbon atoms or trialkylsilyl group; and $R^2$ is a straight chain saturated hydrocarbon group having 1 to 10 carbon atoms or a branched saturated aliphatic hydrocarbon group having 3 to 10 carbon atoms. More preferably, $R^1$ is a straight chain saturated aliphatic hydrocarbon group having 2 to 5 carbon atoms, a branched or cyclic saturated aliphatic hydrocarbon group having 3 to 6 carbon atoms or trimethylsilyl group and $R^2$ is a straight chain saturated hydrocarbon group having 1 to 4 carbon atoms or a branched saturated aliphatic hydrocarbon group having 3 to 4 carbon atoms.

Specific examples of the compounds used as the component (C) include the following compounds.
3-Methyl-3-(trimethoxysilyl)pentane,
3-Methyl-3-(ethoxydimethoxysilyl)pentane,
3-Methyl-3-(isopropoxydimethoxysilyl)pentane,
3-Methyl-3-(butoxydimethoxysilyl)pentane,
3-Methyl-3-(tert-butoxydimethoxysilyl)pentane,
4-Methyl-4-(trimethoxysilyl)heptane,
4-Methyl-4-(ethoxydimethoxysilyl)heptane,
4-Methyl-4-(isopropoxydimethoxysilyl)heptane,
4-Methyl-4-(butoxydimethoxysilyl)heptane,
4-Methyl-4-(tert-butoxydimethoxysilyl)heptane,
5-Methyl-5-(trimethoxysilyl)nonane,
5-Methyl-5-(ethoxydimethoxysilyl)nonane,
5-Methyl-5-(isopropoxydimethoxysilyl)nonane,
5-Methyl-5-(butoxydimethoxysilyl)nonane,
5-Methyl-5-(tert-butoxydimethoxysilyl)nonane,
2,3,4-trimethyl-3-(trimethoxysilyl)pentane,
2,3,4-trimethyl-3-(ethoxydimethoxysilyl)pentane,
2,3,4-trimethyl-3-(isopropoxydimethoxysilyl)pentane,
2,3,4-trimethyl-3-(butoxydimethoxysilyl)pentane,
2,3,4-trimethyl-3-(tert-butoxydimethoxysilyl)pentane,
3,4,5-trimethyl-4-(trimethoxysilyl)heptane,
3,4,5-trimethyl-4-(ethoxydimethoxysilyl)heptane,
3,4,5-trimethyl-4-(isopropoxydimethoxysilyl)heptane,
3,4,5-trimethyl-4-(butoxydimethoxysilyl)heptane,
3,4,5-trimethyl-4-(tert-butoxydimethoxysilyl)heptane,
1,1-dicyclopentyl-1-(trimethoxysilyl)ethane,
1,1-dicyclopentyl-1-(ethoxydimethoxysilyl)ethane,
1,1-dicyclopentyl-1-(isopropoxydimethoxysilyl)ethane,
1,1-dicyclopentyl-1-(butoxydimethoxysilyl)ethane,
1,1-dicyclopentyl-1-(tert-butoxydimethoxysilyl)ethane,
1,1-dicyclohexyl-1-(trimethoxysilyl)ethane,
1,1-dicyclohexyl-1-(ethoxydimethoxysilyl)ethane,
1,1-dicyclohexyl-1-(isopropoxydimethoxysilyl)ethane,
1,1-dicyclohexyl-1-(butoxydimethoxysilyl)ethane,
1,1-dicyclohexyl-1-(tert-butoxydimethoxysilyl)ethane,
1,1-bis(trimethylsilyl)-1-(trimethoxysilyl)ethane,
1,1-bis(trimethylsilyl)-1-(ethoxydimethoxysilyl)ethane,
1,1-bis(trimethylsilyl)-1-(isopropoxydimethoxysilyl)ethane,
1,1-bis(trimethylsilyl)-1-(butoxydimethoxysilyl)ethane,
1,1-bis(trimethylsilyl)-1-(tert-butoxydimethoxysilyl)ethane Among the trialkoxysilane compounds represented by the general formula (1), trimethoxysilane compounds represented by the general formula (6), in which $R^1$ is a straight chain saturated aliphatic group having 2 to 10 carbon atoms or a branched or cyclic saturated aliphatic hydrocarbon group having 3 to 10 carbon atoms and $R^2$ is a methyl group, are novel compounds.

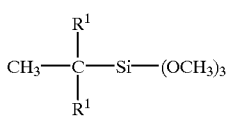

(6)

The novel compounds represented by the general formula (6) can be prepared in a manner similar to that used for the known trialkoxysilane compounds.

An example of the preparation method therefor will be described below.

First, a Grignard reagent represented by the general formula (8)

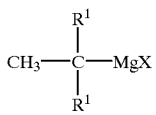

(8)

(wherein X is a halogen atom; and $R^1$ has the same meaning as defined above) is reacted with dichlorosilane to obtain an alkylsilane compound represented by the general formula (9).

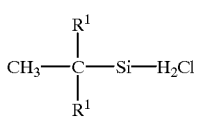

(9)

Then, the compound represented by the general formula (9) is reacted with methanol in the presence of a dehydrohalogenating agent to obtain a compound represented by the general formula (10).

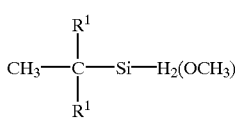

(10)

The compound represented by the general formula (10) is further reacted with methanol in the presence of a catalyst to obtain a compound represented by the general formula (6).

The Grignard reagent represented by the general formula (8), starting compound, can be prepared from corresponding alkyl halide and metallic magnesium by a conventional method.

The reaction between the Grignard reagent represented by the general formula (8) and dichlorosilane can be carried out in ether solvents such as diethyl ether and tetrahydrofuran, hydrocarbon solvents such as hexane and toluene and mixtures thereof at a temperature of −100° C. to 120° C., preferably −78° C. to 100° C.

The reaction between the alkylsilane compound (10) and methanol in a proportion of 1:1 to 10 by mole in the presence of a dehydrohalogenating agent can give rise to the compound (9).

As the dehydrohalogenating agent, there can be used urea, tertiary amines, nitrogen-containing heterocyclic compounds, for example, pyridine, quinoline and isoquinoline. Of these, urea, pyridine and quinoline are preferred. The reaction can be carried out at 0° C. to 120° C. for 5 minutes to 50 hours, preferably at 20° C. to 100° C. for 30 minutes to 6 hours. Upon preparation, solvents may be used. The solvent include organic solvents, for example, hydrocarbons such as pentane, hexane, heptane, octane, nonane and decane, ethers such as diethyl ether, dibutyl ether and tetrahydrofuran, and the like.

The reaction between the compound represented by the general formula (10) and methanol in a molar proportion of 1:2 to 50 in the presence of a dehydrogenation catalyst can yield the trimethoxysilane compound represented by the general formula (6).

As the dehydrogenating catalyst, there can be cited transition metals such as palladium and platinum, organic metal compounds thereof, transient metal carried catalysts such as palladium on carbon, or alkali metals such as potassium and sodium. Of these, palladium on carbon, sodium and the like are preferred. The reaction can be carried out at a temperature of 0° C. to 150° C. for 5 minutes to 50 hours, preferably at 20° C. to 100° C. for 10 minutes to 6 hours.

In the olefin polymerization catalysts of the present invention, the component (C) is used in a molar proportion (component (C)/component (B)) of 0.001 to 5, preferably 0.01 to 1.

The olefins used in the olefin polymerization are generally olefins having up to 12 carbon atoms. Typical example thereof include ethylene, propylene, butene-1,4-methylpentene-1, hexene-1, octene-1 and the like. The catalyst of the present invention is advantageous for stereospecific polymerization of mixtures of these olefins and mixtures of ethylene with a-olefins having 3 carbon atoms. Furthermore, the catalyst of the present invention is effective in stereospecific polymerization of propylene, or mixtures of up to 20 mole % of ethylene or higher α-olefin with propylene, and particularly effective in stereospecific homopolymerization of propylene.

Polymerization Method and Conditions

In practicing polymerization using the catalyst of the present invention, the solid catalyst component (component (A)), organic aluminum compound (component (B)) or silicon compound (component (C)) may be introduced into a polymerization vessel separately or two or all of them may be mixed in advance. However, it is preferred to mix the inert solvent described hereinafter, the organic aluminum compound and the silicon compound, allow the resulting mixture to stand for a predetermined period of time (about 1 minute or longer), contact the mixture with the solid catalyst component, allow the mixture to stand for a predetermined period of time (about 1 minute or longer), and then charge the mixture in a polymerization vessel.

The inert solvent which can be used include alkanes and cycloalkanes such as pentane, hexane, heptane, n-octane, isooctane, cyclohexane and methylcyclohexane; alkyl aromatic hydorcarbons such as toluene, xylene, ethylbenzene, isopropylbenzene, ethyltoluene, n-propylbenzene, diethylbenzene and mono- or dialkylnaphthalene; halogenated or hydrogenated aromatic hydrocarbons such as chlorobenzene, chloronaphthalene, o-dichlorobenzene, tetrahydronaphthalene and decahydronaphthalene; high molecular weight liquid paraffin, or mixtures thereof.

The polymerization of olefins according to the present invention can be carried out at a monomer pressure of atmospheric or superatmospheric pressure. In gas phase polymerization, the monomer pressure should not be lower than the vapor pressure of the olefin to be polymerized at its polymerization temperature and generally is within the range of about 20 to 600 psi.

The polymerization can be carried out either in liquid monomers (olefins) or in gas phases. Further, the polymerization can be performed in any of batch, semicontinuous and continuous methods. Furthermore, the polymerization can be carried out by two or more separate steps of different reaction conditions.

In order to obtain polymers having practically acceptable melt flows, there can be used a molecular weight controlling agent (generally, hydrogen) may co-exist.

The polymerization time is generally from 30 minutes to several hours for batch type methods and is corresponding average dwelling time for continuous methods. For autoclave type reactions, the reaction time typically lasts about 1 to 6 hours.

For slurry methods, the polymerization time is preferably from 30 minutes to several hours. Examples of diluting solvents which are suitable for slurry polymerization include alkanes and cycloalkanes such as pentane, hexane, heptane, n-octane, isooctane, cyclohexane and methylcyclohexane; alkyl aromatic hydrocarbons such as toluene, xylene, ethylbenzene, isopropylbenzene, ethyltoluene, n-propylbenzene, diethylbenzene, and mono- or dialkylnaphthalenes; halogenated and hydrogenated aromatic hydrocarbons such as chlorobenzene, chloronaphthalene, o-dichlorobenzene, tetrahydronaphthalene, and decahydronaphthalene; high molecular weight liquid paraffin; or mixtures thereof; and other diluting solvents well known in the art.

Gas phase polymerization for which the present invention is useful can be performed using a stirring layer reactor system or a fluidized bed reactor system. In a typical gas phase olefin polymerization reactor system, the olefin monomer and the catalyst component are charged into a reaction vessel, which have a stirring equipment. The catalyst components are charged into the reaction vessel through at least one valve controlled port simultaneously or separately. The olefin monomers typically are fed through a gas recycling system which mixes fresh feed monomers and unreacted monomers which are to be removed as waste gas and forces the resulting mixture into the reactor.

Although it is generally unnecessary to do so, the termination of polymerization or inactivation of catalyst upon completion of the polymerization can be performed by contacting the catalyst with water, alcohol or acetone known as a poison or other catalyst inactivating agents.

The polymerization temperature is generally from −10° C. to 180° C. With view to obtaining good catalyst capability and high production rate, preferred temperature is from 20° C. to 100° C., and more preferably 50° C. to 80° C.

Though not essential, it is preferred to carry out preliminary polymerization. In the preliminary polymerization, usually the above-described solid catalyst component (A) is combined with at least a part of the above-described organic aluminum compound component (B) upon use. In this occasion, either a silicon compound or an acetal compound may co-exist. The silicon compound is not limited to those compound used as the catalyst component (C). It is preferred that the concentration of the solid catalyst component (A) in the preliminary polymerization is within the range of usually from 0.01 to 200 mmol as titanium atom per liter of the inert hydrocarbon solvent described hereinbelow.

The amount of the organic aluminum compound component (B) may be such that there can be formed from 0.1 to 500 g, preferably from 0.1 to 300 g, per gram of the solid titanium catalyst component (A). It is preferred that the preliminary polymerization is carried out under mild conditions with addition of olefins and the catalyst component described above to inert hydrocarbon solvents.

The inert hydrocarbon solvent used herein include aliphatic hydrocarbons such as propane, butane, pentane, hexane, heptane, octane, decane, dodecane and kerosene; alicyclic hydrocarbons such as cyclopentane, cyclohexane and methylcyclopentane; aromatic hydrocarbons such as benzene, toluene and xylene, halogenated hydrocarbons such as ethylene chloride and chlorobenzene; or mixtures thereof. Of these inert hydrocarbon solvents, particularly preferred are the aliphatic hydrocarbons. The olefins used in the preliminary polymerization may be the same as or different from the olefins used in the main polymerization described above. The preliminary polymerization may be carried out at a reaction temperature such that the preliminarily produced polymer does substantially not dissolve in the inert hydrocarbon solvent, usually, at about $-10°$ C. to $100°$ C., preferably about $-10°$ C. to $80°$ C. Note that in the preliminary polymerization, molecular weight controlling agents such as hydrogen may be used. The preliminary polymerization may be performed either by a batch method or by a continuous method.

For other conditions such as control method for controlling polymerization and posttreatment, there is no particular limitation specific to the catalyst of the present invention and any conventional methods can be used.

BEST MODE FOR CARRYING OUT THE INVENTION

Hereinafter, the present invention will be described in detail by examples and comparative examples. However, the present invention should not be construed as being limited by what is described below.

In examples and comparative examples, soluble xylene contents (%) of polymer at room temperature (XSRT (%)), polymerization activity, melt flow rates (MFR), and MLMFR at a load of 10 kg were determined in the following manner. Xylene soluble content (%) of polymer at room temperature (XSRT(%)):

A solution of 2 g of polymer in 200 ml of xylene at $135°$ C. was cooled down to room temperature to precipitate polymer, which then was filtered under reduced pressure. The solvent was removed from the filtrate using a rotary evaporator and the product was dried to obtain a residue, the weight of which was measured. XSRT (%) was calculated from the results according to the following equation.

$XSRT\ (\%) = \{(SP - SR)/SP\} \times 100$ wherein $SP$ = gram of sample polymer $SR$ = gram of residue Polymerization Activity
  Calculated according to the following equation.

Polymerization activity (G/g·h)={(gram of polymer obtained)/ (gram of solid catalyst used in polymerization×polymerization time)}

MFR (melt flow rate at a load of 2.16 kg) and MLMFR (melt flow rate at a load of 10 kg): Measured according to JIS K-7210-1995.

The higher the value obtained by dividing MLMFR by MFR (MLMFR/MFR), the broader the molecular weight distribution of the polyolefin.

In each example and comparative example, each compound used in the preparation of the solid catalyst component and polymerization (organic solvent, olefin, hydrogen, titanium compound, magnesium compound, silicon compound and so on) are substantially dehydrated before use and the preparation of the solid catalyst component and polymerization were carried out under the conditions where substantially no water was present and in a nitrogen atmosphere.

The organic aluminum compound and silicon compound used upon polymerization were 1.0M and 0.1M hexane solutions, respectively.

EXAMPLE 1

1) Preparation of Solid Ti Catalyst Component (A)

1.71 g of anhydrous magnesium chloride, 9 ml of decane and 8.4 ml of 2-ethylhexyl alcohol were heated at $130°$ C. for 2 hours to form a homogenous solution. To the solution was added 0.39 g of phthalic anhydride and the resulting mixture was stirred at $130°$ C. for 2 hours to dissolve phthalic anhydride uniformly. The resulting homogeneous solution was cooled down to room temperature and all of it was added dropwise over 1 hour to 72 ml of titanium chloride kept at $-20°$ C. After the addition, the temperature of the resulting mixture was elevated to $110°$ C. over 4 hours, at which temperature 0.95 g of di(2-ethylhexyl) phthalate was added and the mixture was kept at the same temperature for 2 hours with stirring. After the 2 hour reaction was completed, the solids were collected by hot filtration and the solids were resuspended in 72 ml of titanium tetrachloride. Then, the suspension was heated for reaction at $110°$ C. for 2 hours. After completion of the reaction, again hot filtration was conducted to collect solids, which were washed sufficiently with decane and hexane under until no free titanium compound was found in the washings, followed by drying under reduced pressure.

2) Polymerization

In a 1.5-liter stainless steel autoclave were charged 4.8 mg of the solid component prepared by the above-described method, 1.6 ml of 3-methyl-3-(trimethoxysilyl)pentane (component (C)) (0.1M/liter hexane solution), 1.6 ml of triethylaluminum (1M/liter hexane solution), and then 330 g of propylene and 0.38 g of hydrogen. The temperature of the

TABLE 1

|  | component (C) | A (mg) | C (ml) | H$_2$ (g) | polymerization activity (g/g cat-h) | XSRT(%) | MFR (g/10 min) | MLMFR/MFR |
|---|---|---|---|---|---|---|---|---|
| Example 1 | 3-methyl-3-(trimethoxysilyl)pentane | 4.8 | 0.8 | 0.38 | 26,400 | 0.3 | 32 | 25.2 |
| C. Example 1 | dicyclopenthyldimethoxysilane | 5.1 | 0.8 | 0.38 | 22,100 | 1.3 | 12 | 20.1 |
| C. Example 2 | t-butyltrimethoxysilane | 4.9 | 0.8 | 0.38 | 17,600 | 1.6 | 15 | 18.3 |
| C. Example 3 | t-butyl(t-butoxy)dimethoxysilane | 5.3 | 0.8 | 0.38 | 19,200 | 2.2 | 14 | 21.4 |
| C. Example 4 | 1-methylcyclohexyltrimethoxysilane | 5.1 | 0.8 | 0.38 | 16,700 | 2.5 | 17 | 20.4 |

TABLE 2

|  | component (C) | A (mg) | polymerization TEMP. (° C.) | H$_2$ (g) | polymerization activity (g/g cat-h) | XSRT(%) | MFR (g/10 min) | MLMFR/MFR |
|---|---|---|---|---|---|---|---|---|
| Example 2 | 3-methyl-3-(trimethoxysilyl)pentane | 4.8 | 70 | 0.38 | 24,300 | 0.6 | 27 | 26.0 |
| Example 3 | 3-methyl-3-(trimethoxysilyl)pentane | 5.2 | 80 | 0.57 | 28,400 | 0.2 | 80 | 24.2 |
| Example 4 | 3-methyl-3-(trimethoxysilyl)pentane | 4.8 | 80 | 0.76 | 31,600 | 0.2 | 150 | 22.7 |

TABLE 3

|  | component (C) | A (mg) | C (ml) | H$_2$ (g) | polymerization activity (g/g cat-h) | XSRT(%) | MFR (g/10 min) | MLMFR/MFR |
|---|---|---|---|---|---|---|---|---|
| Example 5 | 3-methyl-3-(t-butoxydimethoxysilyl)pentane | 4.4 | 0.8 | 0.38 | 23,100 | 0.5 | 31 | 27.0 |
| Example 6 | 2,3,4-trimethyl-3-(trimethoxysilyl)pentane | 4.7 | 0.8 | 0.38 | 27,400 | 0.4 | 34 | 26.7 |
| Example 7 | 1,1-dicyclopenthyl-1-(trimethoxysilyl)ethane | 5.3 | 0.8 | 0.38 | 24,400 | 0.2 | 29 | 28.1 | autoclave was elevated and the internal temperature thereof was kept at 80° C. After 1 hour, the gas contained in the autoclave was released to terminate the polymerization. Table 1 shows the results obtained (polymerization activity, XSRT, MFR and MLMFR/MFR).

Comparative Examples 1 to 4

The preparation of catalyst and polymerization were performed in the same manner as in Example 1 except that the compound of component (C) was replaced by dicyclopentyldimethoxysilane, tert-butyltrimethoxysilane, tert-butyl(tert-butoxy)dimethoxysilane or 1-methylcyclohexyltrimethoxysilane. Table 1 shows the results obtained.

EXAMPLES 2 TO 4

The preparation of catalyst and polymerization were performed in the same manner as in Example 1 except that the amount of hydrogen used and polymerization temperature were changed to those set forth in Table 2. Table 2 shows the results obtained.

EXAMPLES 5 TO 7

The preparation of catalyst and polymerization were performed in the same manner as in Example 1 except that the compound of component (C) was replaced by 3-methyl-3-(tert-butoxydimethoxysilyl)pentane, 2,3,4-trimethyl-3-(trimethoxysilyl)pentane or 1,1-dicyclopentyl-1-(trimethoxysilyl)ethane. Table 3 shows the results obtained.

EXAMPLE 8

Preparation of 3-methyl-3-(trimethoxysilyl)pentane 8-1) Preparation of 3-methyl-3-(chlorosilyl)pentane In a 300 ml 3-necked flask equipped with a Dimroth condenser and a 100 ml dropping funnel were charged 6.1 g of magnesium and a catalyst amount of iodine, to which were dropwise added 30 g of 3-chloro-3-methylpentane and 63 ml of diethyl ether over 1 hour to obtain a corresponding Grignard reagent. The contents of the flask were cooled down to −78° C. Then, 10 ml of dichlorosilane was bubbled over 30 minutes. After stirring at −78° C. for 1 hour, the reaction mixture was heated under reflux while monitoring the reaction by gas chromatography. The reaction was completed in 9 hours. After cooling, the precipitates formed were filtered and the solvent was evaporated, followed by distilling to afford 15 g of colorless transparent liquid having a boiling point of 145 to 148° C. Yield: 40%.

Mass Spectrometry (EI method): m/z=150 (M⁺)

8-2) Preparation of 3-methyl-3-(methoxysilyl)pentane

In a 300 ml 3-necked flask equipped with a magnetic stirrer, a Dimroth condenser and a 50 ml dropping funnel were charged 50 ml of methanol and 4.5 g of urea. To this was added dropwise 7.3 g of 3-methyl-3-(chlorosilyl) pentane obtained above over 15 minutes. After completion of the addition, the resulting mixture was stirred at room temperature for 1 hour while monitoring the reaction by gas chromatography. After evaporation of methanol, the residue was extracted with 60 ml of hexane. The extraction was repeated 3 times. Then, hexane was distilled off and the residue was used for the following reaction.

8-3) Preparation of 3-methyl-3-(trimethoxysilyl)pentane

In a 300 ml 3-necked flask equipped with a magnetic stirrer, a Dimroth condenser and a 50 ml dropping funnel were charged 50 ml of methanol, about 6 ml of crude solution of 3-methyl-3-(methoxysilyl)pentane obtained above, and a catalytic amount of sodium. The contents of the flask were heated under reflux while monitoring the reaction by gas chromatography. After completion of the reaction, the solvent was distilled off and the product was distilled to obtain 4.1 g of colorless transparent liquid having a boiling point of 187 to 189° C. Yield: 41% (purity by GC analysis: 98%).

Mass Spectrometry (EI method):m/z=206 (M⁺)

| | |
|---|---|
| ¹H-NMR (CD₃Cl): δ (¹H/ppm): | 0.6 (t, 6H), 0.7 (s, 3H), 1.2 (q, 4H), 3.5 (s, 9H); |
| ¹³C-NMR (CD₃Cl): δ (¹³C/ppm): | 50.34, 25.98, 28.52, 20.36, 8.29; |
| ²⁹Si-NMR (CD₃Cl, (Me)₄Si used as chemical shift reference substance): δ (²⁹Si/ppm): | -48.65. |

From the results of analysis described above, the liquid product was confirmed to be 3-methyl-3-(trimethoxysilylmethyl)pentane, the target compound.

ADVANTAGEOUS EFFECTS OF THE INVENTION

As described above, the catalyst for polymerization of olefins and method of preparing polyolefins using the catalyst according to the present invention enable efficient production of polyolefins having a low molecular weight (MFR>20 (g/10 minutes)), a broad molecular weight distribution (MLMFR/MFR>22) and a high stereoregularity when applied to polymerization of olefins having 3 or more carbon atoms.

What is claimed is:

1. A catalyst for polymerizing olefins, comprising:

(A) a solid catalyst component comprising titanium, magnesium and halogen;

(B) an organic aluminum compound; and (C) a silane compound represented by general formula (1)

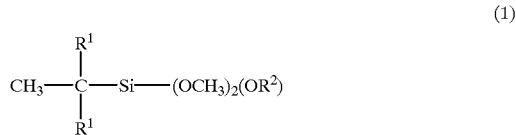

wherein $R^1$ is a straight chain saturated aliphatic hydrocarbon group having 2 or more carbon atoms, a branched or cyclic saturated aliphatic hydrocarbon group having 3 or more carbon atoms or a silyl group; and $R^2$ is a straight chain, branched or cyclic saturated hydrocarbon group.

2. The catalyst as claimed in claim 1, wherein said silane compound is a compound represented by the general formula (1) in which $R^1$ is a straight chain saturated aliphatic hydrocarbon group having 2 to 10 carbon atoms, a branched or cyclic saturated aliphatic hydrocarbon group having 3 to 4. The catalyst as claimed in claim 1, consisting of said 10 carbon atoms or a trialkylsilyl group; and $R^2$ is a straight chain saturated hydrocarbon group having 1 to 10 carbon atoms or a branched saturated aliphatic hydrocarbon group having 3 to 10 carbon atoms.

3. The catalyst as claimed in claims 1 or 2, wherein said silane compound is a silane compound selected from the group consisting of:

3-methyl-3-(trimethoxysilyl)pentane,
3-methyl-3-(tert-butoxydimethoxysilyl)pentane,
4-methyl-4-(trimethoxysilyl)heptane,
2,3,4-trimethyl-3-(trimethoxysilyl)pentane,
3,4,5-trimethyl-4-(trimethoxysilyl)heptane,
1,1-dicyclopentyl-1-(trimethoxysilyl)ethane,
1,1-dicyclohexyl-1-(trimethoxysilyl)ethane, and
1,1-bis(trimethylsilyl)-1-(trimethoxysilyl)ethane. solid catalyst component, said organic aluminum compound, and said silane compound.

* * * * *